(12) United States Patent
Mazzillo et al.

(10) Patent No.: US 11,821,886 B2
(45) Date of Patent: Nov. 21, 2023

(54) SYSTEM AND METHOD FOR DETECTING THE CONCENTRATION OF METAL PARTICLES (71) Applicant: STMICROELECTRONICS S.R.L., Agrate Brianza (IT)

(72) Inventors: Massimo Cataldo Mazzillo, Corato (IT); Antonella Sciuto, S. Giovanni la Punta (IT)

(73) Assignee: STMICROELECTRONICS S.R.L., Agrate Brianza (IT)

(*) Notice: Subject to any disclaimer, the term of this patent is extended or adjusted under 35 U.S.C. 154(b) by 633 days.

(21) Appl. No.: 16/685,618

(22) Filed: Nov. 15, 2019

(65) Prior Publication Data

US 2020/0158710 A1 May 21, 2020

(30) Foreign Application Priority Data

Nov. 16, 2018 (IT) .......................... 102018000010396

(51) Int. Cl.
*H01L 29/872* (2006.01)
*G01N 33/20* (2019.01)
*G01N 27/414* (2006.01)

(52) U.S. Cl.
CPC ........... *G01N 33/20* (2013.01); *G01N 27/414* (2013.01); *H01L 29/872* (2013.01)

(58) Field of Classification Search
CPC .................................................. G01N 27/129
See application file for complete search history.

(56) References Cited

U.S. PATENT DOCUMENTS

| 9,806,216 | B2 | 10/2017 | Mazzillo | |
|---|---|---|---|---|
| 2004/0108530 | A1* | 6/2004 | Sandvik | H01L 31/02322 257/E31.086 |
| 2013/0153919 | A1* | 6/2013 | Curatola | H01L 21/743 257/E21.403 |
| 2013/0291627 | A1 | 11/2013 | Hu et al. | |
| 2014/0077311 | A1* | 3/2014 | Simin | H01L 29/861 257/487 |
| 2016/0260861 | A1* | 9/2016 | Mazzillo | H01L 31/1812 |
| 2016/0349108 | A1* | 12/2016 | Mazzillo | H01L 31/108 |
| 2017/0018674 | A1* | 1/2017 | Mazzillo | G01J 5/22 |

(Continued)

FOREIGN PATENT DOCUMENTS

JP 2001-281213 A 10/2001

OTHER PUBLICATIONS

Kaufmann et al., "Characterization of a SiC MIS Schottky diode as RBS particle detector," *Journal of Instrumentation* 13( P02017):1-13, 2018 (15 pages).

(Continued)

*Primary Examiner* — Sarah K Salerno
(74) *Attorney, Agent, or Firm* — SEED IP LAW GROUP LLP (57) ABSTRACT

A system for detecting the concentration of metal particles of at least one first material, which includes a detector with: a semiconductor body including a cathode region, delimited by a front surface; and an anode structure made of metal material, which extends over a part of the cathode region, leaving part of the front surface exposed. The anode structure and the part of the cathode region form a first contact of a Schottky type. The exposed part of the front surface can access the metal particles.

23 Claims, 5 Drawing Sheets (56) References Cited

U.S. PATENT DOCUMENTS

2017/0271158 A1* 9/2017 Minamisawa ...... H01L 21/0485
2019/0040545 A1* 2/2019 Nakamura .............. C30B 29/36

OTHER PUBLICATIONS

Sato et al., "Rapid Detection and Element Identification of Fine Metal Particles for Underpinning Battery Quality—X-ray Particle Contaminant Analyzer EA8000-," *Hitachi Review* vol. 65 (2016), No. 7 (5 pages).
So et al., "Interdigitated Pt-GaN Schottky interfaces for high-temperature soot-particulate sensing," *Applied Surface Science* 368:104-109, 2016 (6 pages).

* cited by examiner

SYSTEM AND METHOD FOR DETECTING THE CONCENTRATION OF METAL PARTICLES

BACKGROUND

Technical Field

The present disclosure relates to a system and a method for detecting the concentration of metal particles.

Description of the Related Art

Today, in numerous contexts there is felt the need to monitor the concentration of metal particles.

For example, the need to control the amount of metal particles present in the air arises in the industrial field, and in particular within industrial plants in which production processes are carried out to manufacture devices that might get damaged by the presence of an excess of metal particles dispersed in the air. Likewise, this need also arises in the context of laser processing of metal materials, where the interaction between high-energy laser pulses and metal workpieces causes emission, by these metal workpieces, of metal clusters. Once again by way of example, sensors for detecting the concentration of metal particles also find application in the field of monitoring of exhaust gases of combustion engines.

This being said, currently, monitoring of the concentration of particles is generally carried out using particularly cumbersome and/or costly equipment, such as equipment that makes it possible to carry out a chemico-spectral analysis by means of inductively coupled plasma (ICP) or else scanning electron microscopy and energy-dispersive X-ray spectroscopy (SEM-EDX).

BRIEF SUMMARY

At least one embodiment of the present disclosure is a system for detecting the concentration of metal particles that will overcome at least in part the drawbacks of the known art.

According to the present disclosure, a system and a method for detecting the concentration of metal particles are provided.

BRIEF DESCRIPTION OF THE SEVERAL VIEWS OF THE DRAWINGS

For a better understanding of the present disclosure, preferred embodiments thereof are now described, purely by way of non-limiting example and with reference to the attached drawings, wherein.

DETAILED DESCRIPTION

Figure 1:
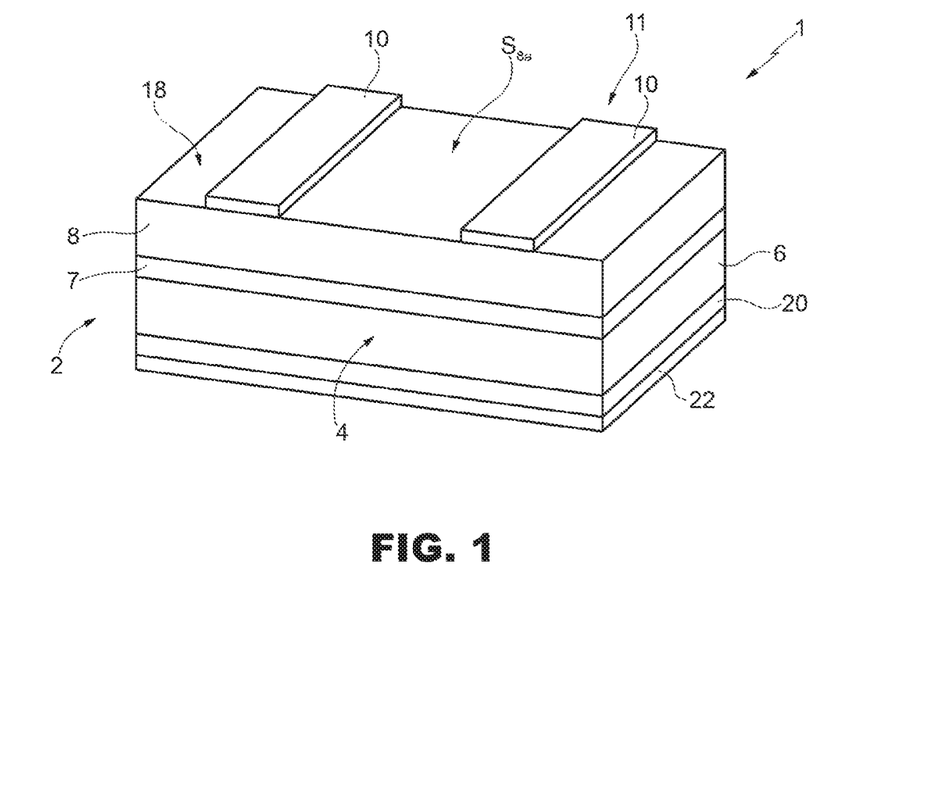
FIG. 1 is a schematic perspective view of a detector.

FIG. 1 shows a detector 1, which is formed in a first die 2 of semiconductor material, which in turn comprises a semiconductor body 4, made, for example, of silicon carbide, and in particular of the so-called 4H-polytype silicon carbide (4H—SiC).

In greater detail, the semiconductor body 4 comprises a substrate 6 of an N+ type (for example, doped with nitrogen), which has a doping level of, for example, $1 \times 10^{19}$ cm$^{-3}$ and a thickness of, for example, 350 µm. Moreover, the semiconductor body 4 comprises a buffer epitaxial layer 7 and a front epitaxial layer 8.

The buffer epitaxial layer 7 extends over the substrate 6 and is in direct contact with the latter. Moreover, the buffer epitaxial layer 7 is of an N type, has a doping level comprised, for example, between $5 \times 10^{15}$ cm$^{-3}$ and $5 \times 10^{16}$ cm$^{-3}$ and has a thickness comprised, for example, between 0.3 µm and 1 µm.

The front epitaxial layer 8 is of an N-type, has a doping level lower than $1 \times 10^{14}$ cm$^{-3}$ (for example, $8 \times 10^{13}$ cm$^{-3}$) and a thickness, for example, of between 4 µm and 8 µm. The front epitaxial layer 8 is delimited at the top by a first surface $S_{8a}$.

The detector 1 further comprises a plurality of anode regions 10 (two of which are shown in FIG. 1), which are made of nickel silicide ($Ni_2Si$) and extend over the first surface $S_{8a}$, in contact with the front epitaxial layer 8. The anode regions 10 have a thickness of, for example, (approximately) 200 nm. In greater detail, the anode regions 10 are the same as one another and have the shape of a parallelepiped. In addition, the anode regions 10 are arranged so that the corresponding parallelepipeds have one and the same orientation. Moreover, the anode regions 10 are laterally staggered with respect to one another so as to leave portions of the first surface $S_{8a}$ exposed.

In practice, the anode regions 10 form, as a whole, an anode structure 11, which extends on the front epitaxial layer 8 and is patterned so as to leave exposed portions of the front epitaxial layer 8, which will be referred to in what follows, as a whole, as "exposed structure 18". The exposed structure 18 is accessible to the metal particles; i.e., the latter can contact the exposed structure 18.

Extending underneath the substrate 6, and in direct contact with the latter, is a region 20, which will be referred to hereinafter as "bottom contact region 20". The bottom contact region 20 is made of nickel silicide and has a thickness of, for example, approximately 200 nm.

The detector 1 further comprises a bottom multilayer structure 22, arranged underneath the bottom contact region 20 and in contact with the latter. The bottom multilayer structure 22 may be formed by a succession of corresponding three layers, which are respectively made, for example, of titanium (Ti), nickel (Ni), and gold (Au) and have respective thicknesses of, for example, 400 nm, 100 nm, and 50 nm. The bottom multilayer structure 22 functions as bottom metallization, and in particular as cathode metallization.

The detector 1 further comprises a top metallization (not shown) that contacts the anode regions 10, which can hence be biased at one and the same voltage.

In practice, the anode regions 10 and the front epitaxial layer 8 form a first metal-semiconductor junction of a rectifying type, i.e., characterized by the presence of a Schottky barrier. The front epitaxial layer 8 forms the cathode region of this first metal-semiconductor junction. Moreover, the substrate 6 and the bottom contact region 20 form a second metal-semiconductor junction, of a non-rectifying type; i.e., they form a so-called ohmic contact. Without any loss of generality, the detector 1 may be manufactured by implementing the process described in U.S. Pat. No. 9,806,216.

Figure 2:
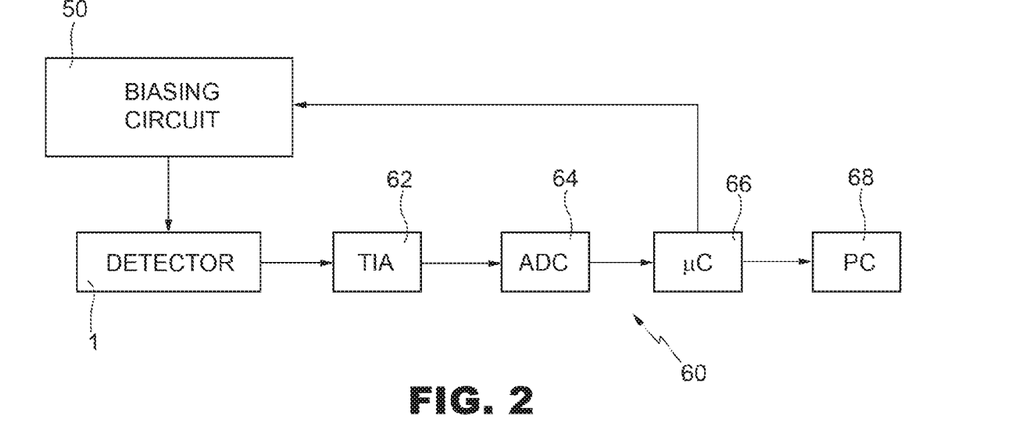
FIG. 2 shows a block diagram of a system for detecting the concentration of metal particles.

As shown in FIG. 2, the detector 1 can be coupled to a biasing circuit 50, which can be controlled so as to impose a voltage $V_{pol}$ between the top metallization and the bottom multilayer structure 22. The voltage $V_{pol}$ forward biases the aforementioned first metal-semiconductor junction.

This being said, the detector 1 has an electrical behavior similar to that of a diode. Moreover, the present Applicant has noted how, by varying the concentration of metal particles arranged on the anode structure 11, and hence also on the exposed structure 18, there occurs a variation of the electrical behavior of the detector 1, and in particular of the current vs. voltage curve that characterizes the detector 1.

Figure 3:
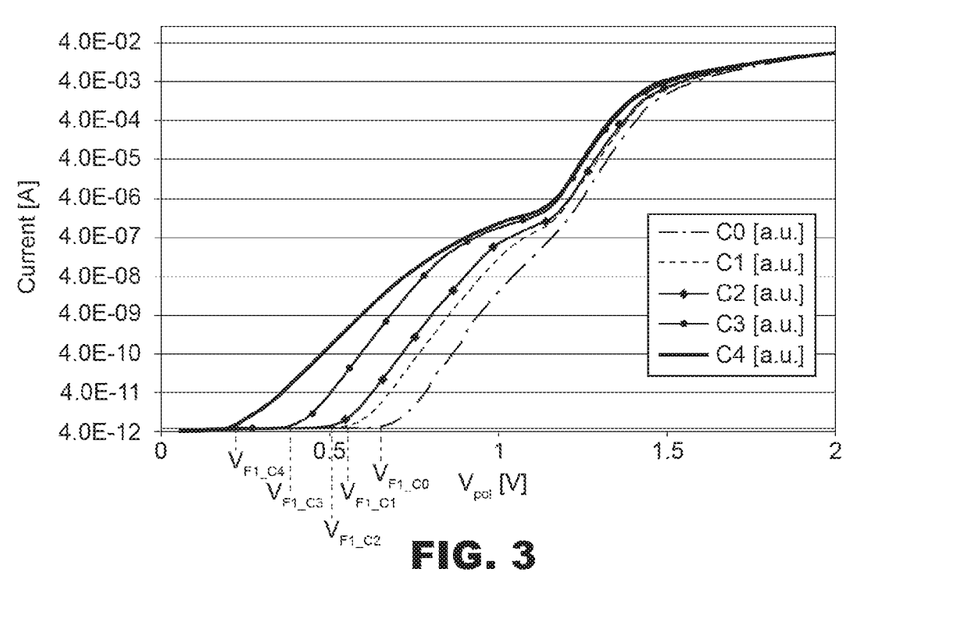
FIG. 3 shows a diagram representing current vs. voltage curves, for different values of concentration of metal particles.

In greater detail, FIG. 3 shows examples of curves that indicate the relation between the voltage $V_{pol}$ and the current that flows through the detector 1, between the top metallization and the bottom multilayer structure 22; each curve refers to a corresponding concentration of metal particles (for example, of tantalum) deposited on the exposed structure 18; these (rising) concentrations are denoted respectively by C0-C4, where C0 is a zero concentration.

In practice, the curves shown in FIG. 3 highlight a threshold behavior, since, in each curve, the current assumes non-zero values only when the voltage $V_{pol}$ exceeds a respective threshold value, designated, respectively, by $V_{F1\_C0}, \ldots, V_{F1\_C4}$.

Figure 4:
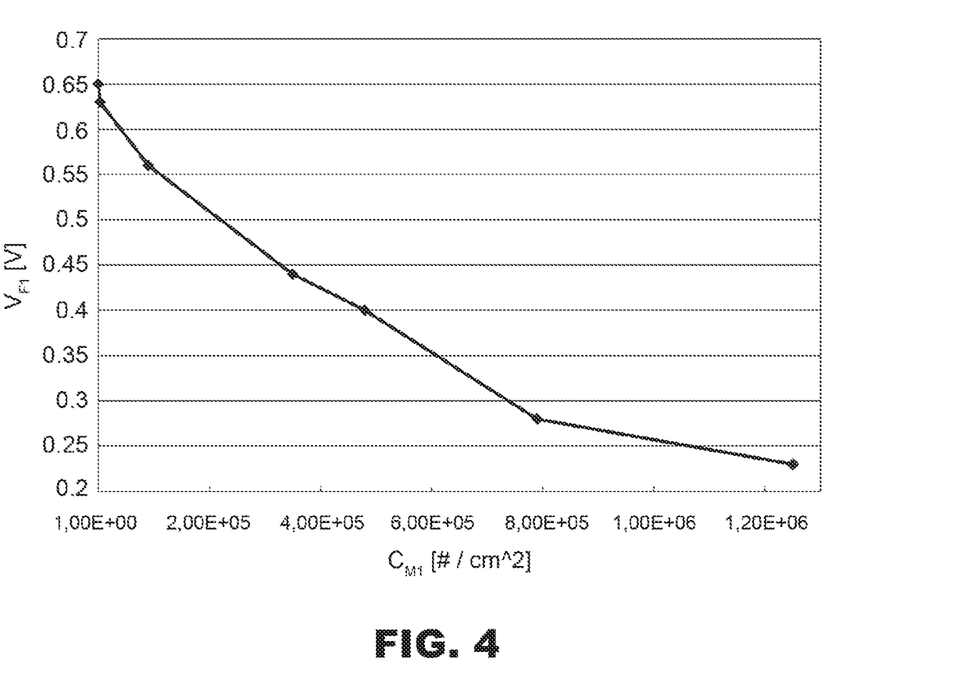
FIG. 4 shows an example of plot of a cut-in voltage of a detector, as a function of the concentration of metal particles.

In practice, if we denote generically as "cut-in voltage $V_{F1}$" the aforementioned threshold value, the present applicant has noted that, as shown in FIG. 4, the cut-in voltage $V_{F1}$ decreases as the concentration of the metal particles deposited on the exposed structure 18 (denoted generically by $C_{M1}$ and expressed as number of particles per square centimeter, and on the hypothesis of the particles being approximately spherical with average radius of, for example, 1 μm) increases.

The present Applicant has moreover noted that, if the anode structure 11 were to cover entirely the front epitaxial layer 8, and hence if the exposed structure 18 were absent, the current vs. voltage curve would be independent of the concentration of metal particles present on the anode structure 11. Moreover, given the large thickness of the anode regions 10, the presence of metal particles thereon deposited does not affect the current vs. voltage curve.

In practice, as mentioned previously, the aforesaid first metal-semiconductor junction, formed by the anode structure 11 and by the front epitaxial layer 8, forms a first Schottky contact, characterized by a fixed cut-in voltage, which does not depend upon the concentration of deposited metal particles and is equal to the voltage $V_{F1\_C0}$. In addition, the metal particles present on the exposed structure 18 form the anode of a second Schottky contact, characterized by a variable cut-in voltage (the aforementioned cut-in voltage $V_{F1}$), which is lower than the fixed cut-in voltage and decreases as the concentration of deposited metal particles increases. Moreover, the higher the fixed cut-in voltage, the wider the range in which it is possible to modulate the variable cut-in voltage, thus increasing the sensitivity of the detector 1.

In greater detail, deposition of metal particles on the exposed structure 18 causes generation of local reductions of the cut-in voltage (equivalently, of the so-called barrier height), which occur in the current vs. voltage curve. In fact, the contact regions between the metal particles and the exposed structure 18 function as sinker regions for the flow of carriers that move from the semiconductor towards the metal. This effect depends upon the type of semiconductor, the geometry of the exposed structure 18, the type of metal particles and their concentration on the exposed structure 18, whereas it is independent of the concentration of the metal particles on the anode regions 10.

In even greater detail, considering an anode region 10, the junction that forms the aforementioned first Schottky contact has a respective depleted region, which extends not only in the portion of front epitaxial layer 8 arranged in contact with the anode region 10, but also in laterally adjacent portions, i.e., in exposed portions of the front epitaxial layer 8. Consequently, in these exposed portions of the front epitaxial layer 8 an electric field is present. Hence, the diode behavior of the detector 1 is affected by the concentration of metal particles that contact the exposed portions of the front epitaxial layer 8.

For practical purposes, the fact that the anode structure 11 is made of nickel silicide and the front epitaxial layer 8 is made of silicon carbide guarantees formation of a relatively high energy barrier, enabling detection of metal particles made of any material that forms, with silicon carbide, a lower barrier.

Once again with reference to FIG. 2, the detector 1 may form a detection system 60, which further comprises an amplification circuit 62, which is formed by a transimpedance amplifier and is coupled to the detector 1 so as to receive the current generated by the latter to generate a corresponding output voltage. In addition, the detection system 60 comprises an analog-to-digital converter 64, a microcontroller unit 66, and a computer 68.

The analog-to-digital converter 64 receives the output voltage and generates a corresponding digital voltage, which once again represents the current generated by the detector 1 and is supplied to the microcontroller unit 66, which, as described hereinafter, generates and sends to the computer 68 a corresponding estimation signal, representing an estimate of the concentration of metal particles on the detector 1. The computer 68 enables a user to display this estimate of the concentration of metal particles.

In detail, the microcontroller unit 66 stores a data structure (for example, a look-up table), contained in which are calibration data. For example, the microcontroller unit 66 stores a calibration curve given by a plurality of calibration values $C_{M1'}$ of the concentration of metal particles, which are associated with corresponding calibration values $V_{F1'}$ of the cut-in voltage $V_{F1}$. In general, the calibration data depend, as mentioned previously, upon the geometry of the first Schottky contact and upon the geometry of the exposed structure 18, as well as upon the metal material constituting the particles.

Figure 5:
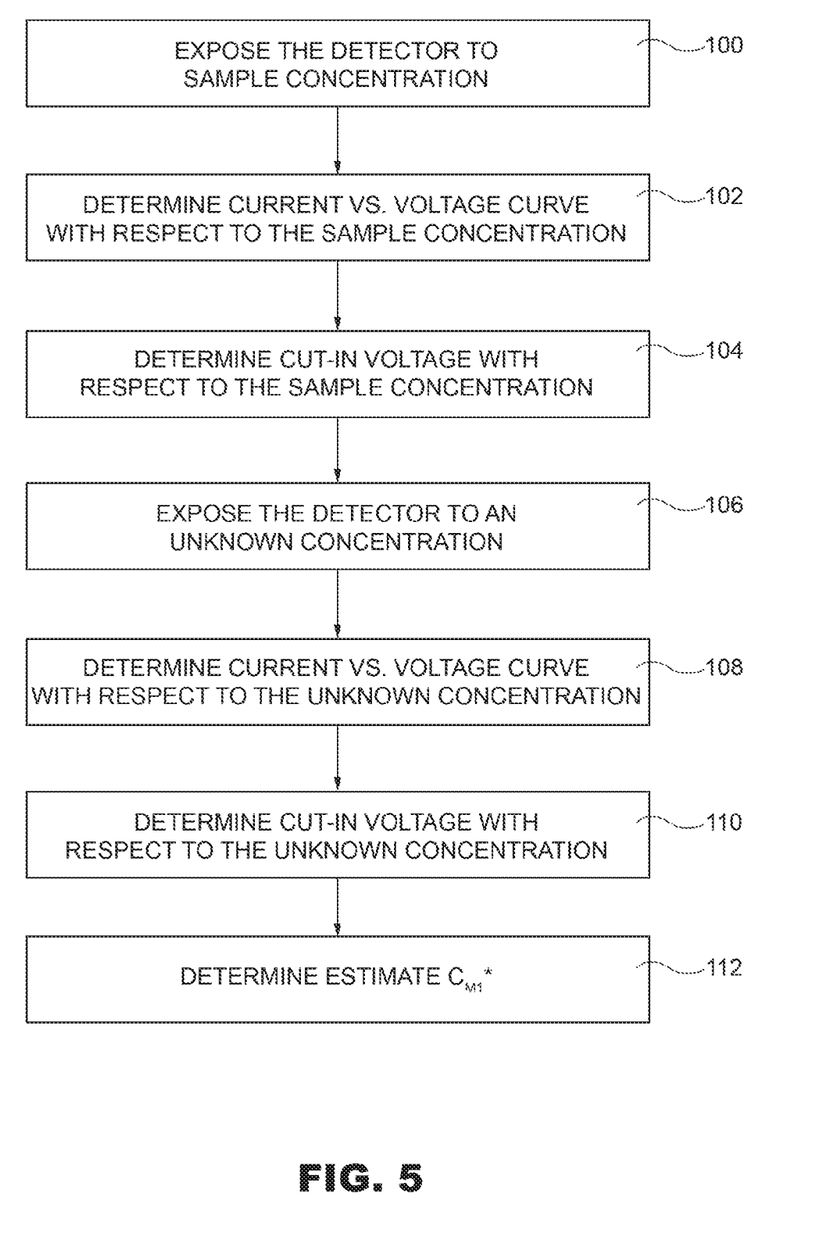
FIGS. 5 and 8 show flowcharts of operations performed by the present detection system.

In practice, it is possible to carry out the operations shown in FIG. 5.

In detail, a calibration procedure is carried out, which envisages pre-arranging a plurality of powders (distributions) of metal particles, each of which has a concentration equal to one of the aforementioned concentration-calibration values $C_{M1'}$; in what follows these concentration-calibration values $C_{M1'}$ will be referred to as "sample concentrations $C_{M1'}$".

This being said, the detector 1 is exposed (block 100), in succession, to powders of metal particles having concentrations equal to the sample concentrations $C_{M1'}$.

For each sample concentration $C_{M1'}$, the microcontroller unit 66 determines (block 102) a corresponding current vs. voltage curve of the detector 1. In greater detail, the microcontroller unit 66 co-operates with the biasing circuit 50 so as to vary the voltage $V_{pol}$ and determine the corresponding current vs. voltage curve, on the basis of the current generated by the detector 1.

Next, for each current vs. voltage curve, and hence for each sample concentration $C_{M1'}$, the microcontroller unit 66 determines (block 104) the corresponding value of calibration $V_{F1'}$ of the cut-in voltage $V_{F1}$, which is, for example, equal to the voltage value $V_{pol}$ for which the current exceeds a threshold value.

Once calibration is through, the detector 1 can be exposed (block 106) to a distribution of metal particles having an unknown concentration. In these conditions, the microcontroller unit 66 determines (block 108) a corresponding current vs. voltage curve; next, on the basis of this current vs. voltage curve, the microcontroller unit 66 determines (block 110) the corresponding value $V_{F1*}$ of the cut-in voltage. Finally, the microcontroller unit 66 determines (block 112) an estimate $C_{M1*}$ of the unknown concentration of metal particles, comparing the value $V_{F1*}$ with the calibration curve stored.

Next, the metal particles deposited on the exposed structure 18 can be removed, for example, by carrying out a wet etch, in order to enable a new measurement.

The detection system 60 can be used also in the case where the particles are constituted by two or more materials, instead of by a single metal material.

Figure 6:
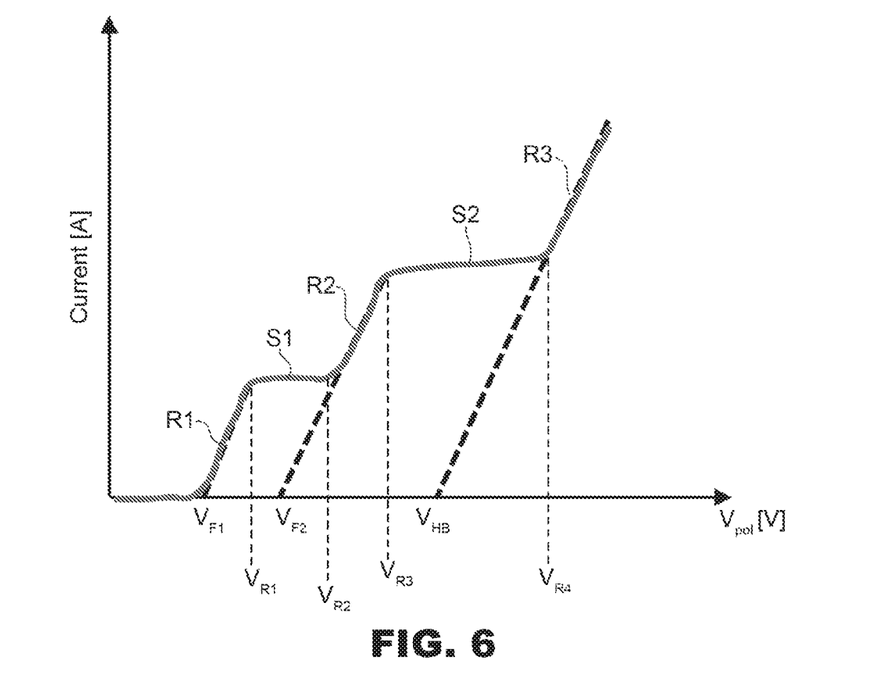
FIG. 6 shows a current vs. voltage plot, in the presence of metal particles of two different types.

In detail, in the case where the detector 1 comes into contact with particles of a first type and a second type, of a first metal material and a second metal material, respectively, the current vs. voltage curve of the detector 1 assumes a plot of the type shown in FIG. 6.

In particular, the current vs. voltage curve shown in FIG. 6 is characterized by the presence of three thresholds, due to the presence of three contacts. In fact, in addition to the aforementioned first Schottky contact, formed between the anode structure 11 and the front epitaxial layer 8, the receiver 1 includes the aforementioned second Schottky contact, which originates from the contact between the particles of the first type and the exposed structure 18, and a third Schottky contact, which originates from the contact between the particles of the second type and the exposed structure 18. In particular, the particles of the second type that contact the exposed structure 18 form the anode of the third Schottky contact, the cathode of which is formed by the part of exposed structure 18 contacted thereby. Moreover, as already said for the second Schottky contact, also the third Schottky contact is characterized by a corresponding variable cut-in voltage, which depends upon the concentration of the particles of the second type arranged on the exposed structure 18.

This being said, in FIG. 6, the (fixed) built-in voltage of the first Schottky contact is designated by $V_{HB}$, whereas the (variable) cut-in voltage of the second Schottky contact is once again denoted by $V_{F1}$; the (variable) cut-in voltage of the third Schottky contact is designated by $V_{F2}$. Moreover, FIG. 6 regards a respective pair of concentrations of the metal particles of the first and second types and shows how the voltage $V_{HB}$ is higher than the voltages $V_{F1}$, $V_{F2}$; moreover, purely by way of example, the voltage $V_{F2}$ is higher than the voltage $V_{F1}$.

In greater detail, the current vs. voltage curve shown in FIG. 6 is zero until the voltage $V_{pol}$ exceeds the voltage $V_{F1}$; then, the curve exhibits:

- a first portion with high slope (designated by R1), which has an approximately linear increasing plot (in semilogarithmic scale) and extends between the voltage $V_{F1}$ and a voltage $V_{R1}$;
- a first portion with low slope (designated by S1), which extends between the voltage $V_{R1}$ and a voltage $V_{R2}$, higher than the voltage $V_{F2}$, and has a slightly increasing linear plot (in semilogarithmic scale) that is to a first approximation constant;
- a second portion with high slope (designated by R2), which has an approximately linear increasing plot (in semilogarithmic scale) and extends between the voltage $V_{R2}$ and a voltage $V_{R3}$, lower than the voltage $V_{HB}$;
- a second portion with low slope (designated by S2), which extends between the voltage $V_{R3}$ and a voltage $V_{R4}$, higher than the voltage $V_{HB}$, and has a slightly increasing linear plot (in semilogarithmic scale) that is to a first approximation constant; and
- a third portion with high slope (designated by R3), which has an approximately linear increasing plot (in semilogarithmic scale) and extends starting from the voltage $V_{R4}$.

In even greater detail, FIG. 6 shows how the cut-in voltage $V_{F1}$ of the second Schottky contact represents a first threshold of the current vs. voltage curve. The cut-in voltage $V_{F2}$ of the third Schottky contact represents a second threshold of the current vs. voltage curve and is equal to the voltage that is obtained by linearly prolonging the second portion with high slope R2 until a zero current is obtained. Finally, the fixed cut-in voltage $V_{HB}$ represents a third threshold and is equal to the voltage that is obtained by linearly prolonging the third portion with high slope R3 until a zero current is obtained.

Figure 7:
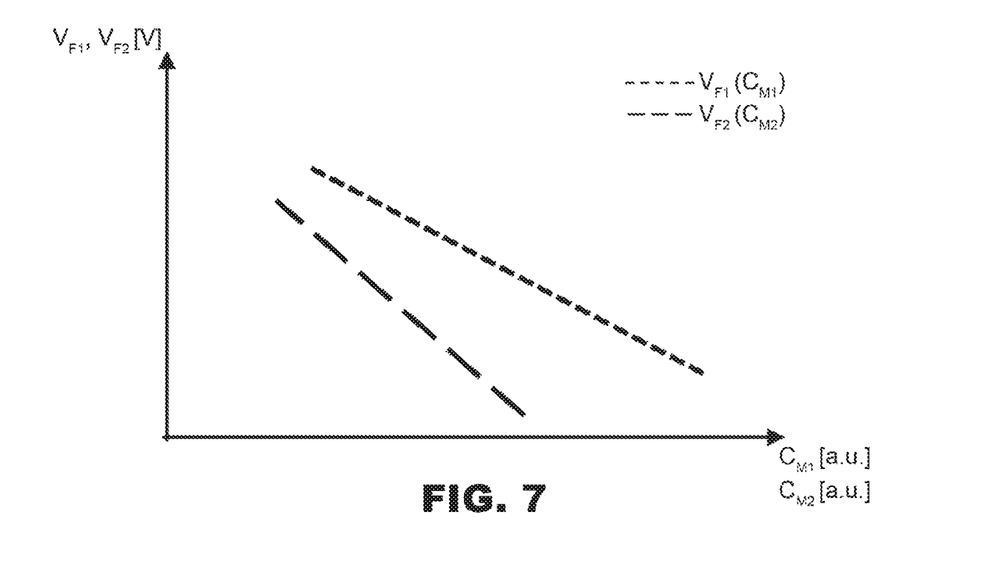
FIG. 7 shows a diagram which plots two cut-in voltages, one as a function of a first concentration of metal particle, and the other as a function of a second concentration of metal particles.

This being said, the present Applicant has noted how, if we denote the concentrations of the metal particles of the first and second types deposited on the exposed structure 18, respectively, as $C_{M1}$ and $C_{M2}$, the voltage $V_{F1}$ decreases as the concentration $C_{M1}$ increases, and the voltage $V_{F2}$ decreases as the concentration $C_{M2}$ increases, as shown qualitatively in FIG. 7. In addition, the voltage $V_{F1}$, and hence the cut-in voltage of the second Schottky contact, is to a first approximation independent of the concentration $C_{M2}$. Likewise, the voltage $V_{F2}$, and hence the cut-in voltage of the third Schottky contact, is to a first approximation independent of the concentration $C_{M1}$.

This being said, it is possible to carry out a calibration procedure, which envisages exposing the detector 1 to different concentrations of the particles of the first and second types.

Figure 8:
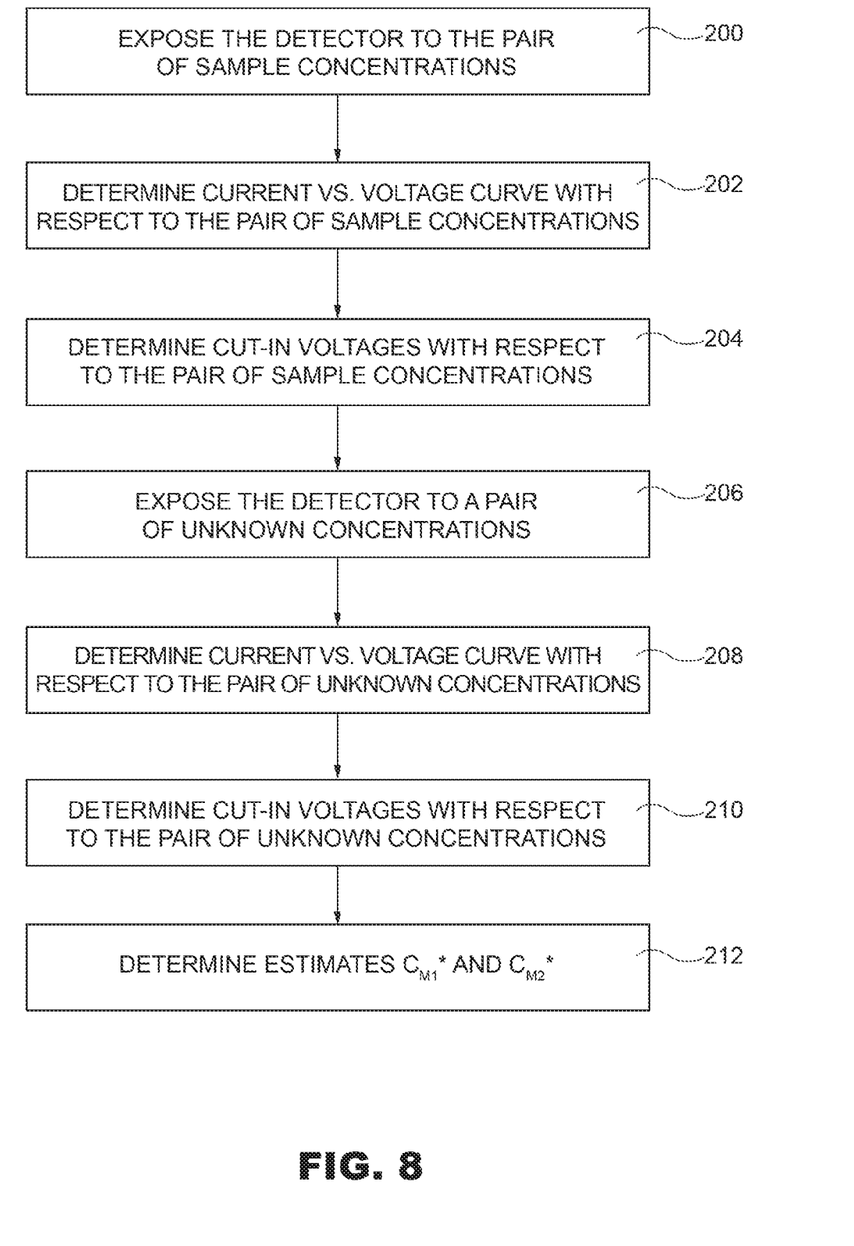

For example, as shown in FIG. 8, the detector 1 is exposed (block 200) to a plurality of calibration powders, each calibration powder being formed by a corresponding mixture of particles of the first type and of the second type and hence being characterized by a corresponding pair of values of calibration $C_{M1'}$, $C_{M2'}$ of the concentrations of the metal particles of the first and second types, which in what follows will be referred to as "pair of sample concentrations $C_{M1'}$, $C_{M2'}$".

For each calibration powder, and hence for each pair of sample concentrations $C_{M1'}$, $C_{M2'}$, the microcontroller unit 66 determines (block 202) a corresponding current vs.

voltage curve of the detector 1. In greater detail, the microcontroller unit 66 co-operates with the biasing circuit 50 so as to vary the voltage $V_{pol}$ and determine the corresponding current vs. voltage curve, on the basis of the current generated by the detector 1.

Next, for each current vs. voltage curve, and hence for each pair of sample concentrations $C_{M1'}$, $C_{M2'}$, the microcontroller unit 66 determines (block 204) the corresponding values $V_{F1'}$, $V_{F2'}$ of the cut-in voltages $V_{F1}$, $V_{F2}$, which in what follows will be referred to as "pair of calibration values $V_{F1'}$, $V_{F2'}$". As explained previously, the calibration value $V_{F1'}$ is, for example, equal to the voltage value $V_{pol}$ for which the current exceeds a threshold value. Moreover, the calibration value $V_{F2'}$ depends upon the evolution of the second portion with high slope R2 and is obtained by prolonging mathematically the second portion with high slope R2 downwards, up to intersection of the zero-current axis; the calibration value $V_{F2'}$ may be set equal to the voltage value corresponding to the intersection.

The calibration procedure enables the microcontroller unit 66 to store, for each pair of sample concentrations $C_{M1'}$, $C_{M2'}$, the corresponding pair of calibration values $V_{F1'}$, $V_{F2'}$. In greater detail, the microcontroller unit 66 may store a first calibration curve, which correlates the calibration values $V_{F1'}$ to the corresponding sample concentrations $C_{M1'}$, and a second calibration curve, which correlates the calibration values $V_{F2'}$ to the corresponding sample concentrations $C_{M2'}$.

Variants of the calibration procedure are, however, possible. For example, the detector 1 may be exposed, instead of to known mixtures, to known powders consisting of just one type of particles. For instance, the detector 1 may be exposed, in succession, to a plurality of powders of particles of the first type with concentrations equal to the aforementioned sample concentrations $C_{M1'}$ so that it can determine the corresponding calibration values $V_{F1'}$. Next, the detector 1 is exposed, in succession, to a plurality of powders of particles of the second type with concentrations equal to the aforementioned sample concentrations $C_{M2'}$ so that it can determine the corresponding calibration values $V_{F2'}$. This calibration operation substantially yields the same results as the operations made in blocks 100-104.

Then, the detector 1 may be exposed (block 206) to an unknown mixture of metal particles of the first and second types, which is characterized by a pair of unknown concentrations. In these conditions, the microcontroller unit 66 determines (block 208) a corresponding current vs. voltage curve. Next, on the basis of this current vs. voltage curve, the microcontroller unit 66 determines (block 210) the corresponding pair of values $V_{F1*}$, $V_{F2*}$ of the cut-in voltages $V_{F1}$, $V_{F2}$.

Finally, the microcontroller unit 66 determines (block 212) the estimates $C_{M1*}$ and $C_{M12*}$ of the unknown concentrations of the metal particles of the first and second types, comparing the values $V_{F1*}$ and $V_{F2*}$, respectively, with the first and second calibration curves stored.

From what has been described and illustrated previously, the advantages that the present solution affords emerge clearly.

In particular, the present system enables determination in an inexpensive way of the concentration of metal particles. The measurement is based on the modulation, as a function of the concentration/concentrations, of one or more cut-in voltages of the detector 1, which hence functions as sensor. From an energy standpoint, the measurement is based on the modulation of the barrier height of one or more Schottky contacts, as a function of the concentration of one or more distributions of metal particles.

In addition, the present system is based upon a compact detector, which is simple to manufacture and capable of operating at high temperatures and/or in the presence of radiation.

In conclusion, it is clear that modifications and variations may be made to what has been described and illustrated so far, without thereby departing from the sphere of protection of the present disclosure.

For example, the semiconductor body, instead of being made of silicon carbide, may be made of a different semiconductor material, such as a semiconductor chosen from among gallium nitride (GaN), silicon (Si), or gallium aluminum nitride (AlGaN).

The anode regions 10 may be made of a metal material different from the one described.

As regards the bottom contact region 20, it may be absent, in which case the bottom multilayer structure 22 directly contacts the substrate 6. Likewise, also the buffer epitaxial layer 7 may be absent. More in general, the detector 1 may have a shape and/or structure different from the one described. Moreover, the types of doping may be reversed as compared to what has been described.

Finally, it is possible for the microcontroller unit 66 to determine the estimate of the concentration on the basis of an electrical quantity other than the variable cut-in voltage, such as the corresponding barrier height, which is in any case correlated to the cut-in voltage. In this case, the microcontroller unit 66 stores corresponding calibration data.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system for detecting a concentration of metal particles of a first material, the system comprising a detector including:
   a contact;
   a semiconductor body on the contact, the semiconductor body including:
   a substrate;
   a first epitaxial layer on the substrate, the first epitaxial layer being a doped layer having a first thickness; and
   a second epitaxial layer on the first epitaxial layer and including a cathode region and a front surface, the second epitaxial layer being a doped layer having a second thickness greater than the first thickness; and
   an anode structure of a conductive material, the anode structure including a plurality of anode regions that extend on and in physical contact with parts of the front surface of the second epitaxial layer, wherein the plurality of anode regions have the same orientation and are laterally staggered such that parts of the front surface of the second epitaxial layer are left exposed, wherein the anode structure and the second epitaxial layer form a Schottky contact, and wherein the parts of the front surface of the second epitaxial layer left exposed are accessible to the metal particles.

2. The system according to claim 1, wherein the detector is configured to generate, when subjected to a biasing voltage and, in the presence of the metal particles of the first material, a current that depends upon the concentration of the metal particles of the first material on the parts of the front surface of the second epitaxial layer left exposed.

3. The system according to claim 2, further comprising a processing unit electrically coupled to the detector and configured to determine, based on the current, a first estimate indicating the concentration of the metal particles of the first material on the parts of the front surface of the second epitaxial layer left exposed.

4. The system according to claim 3, wherein:
the current has a profile, as the biasing voltage of the detector varies, that includes a first variable threshold having a position that depends upon the concentration of the metal particles of the first material on the parts of the front surface of the second epitaxial layer left exposed; and
the processing unit is configured to determine a first quantity indicative of the position of the first variable threshold and to determine said first estimate as a function of said first quantity.

5. The system according to claim 4, wherein the processing unit is configured to store calibration data that associate sample values of concentration with corresponding sample threshold values, and to compare said first quantity with said calibration data.

6. The system according to claim 4, wherein the profile of the current also includes a fixed threshold, which depends upon said Schottky contact and is equal to a value of biasing voltage greater than the first variable threshold.

7. The system according to claim 4, wherein:
the profile of the current includes a second variable threshold in the presence of metal particles of a second material, the second variable threshold having a position that depends upon a concentration of the metal particles of the second material on the parts of the front surface of the second epitaxial layer left exposed; and
the processing unit is configured to determine a second quantity, indicative of the position of the second variable threshold, and determine, as a function of the second quantity, a second estimate, indicative of the concentration of metal particles of the second material on the parts of the front surface of the second epitaxial layer left exposed.

8. The system according to claim 1, wherein the cathode region is formed by a material chosen from among: silicon carbide, gallium nitride, silicon, or gallium aluminum nitride.

9. The system according to claim 1, wherein the anode structure is made of nickel silicide.

10. A method for detecting a concentration of metal particles, comprising:
arranging a detector in contact with metal particles of a first material, the detector including:
a contact;
a semiconductor body on the contact, the semiconductor body including:
a substrate;
a first epitaxial layer on the substrate, the first epitaxial layer being a doped layer having a first thickness; and
a second epitaxial layer on the first epitaxial layer and including a cathode region and a front surface, the second epitaxial layer being a doped layer having a second thickness greater than the first thickness; and
an anode structure made of a conductive material, the anode structure including a plurality of anode regions that extend on and in physical contact with parts of the front surface of the second epitaxial layer, wherein the plurality of anode regions have the same orientation and are laterally staggered such that parts of the front surface of the second epitaxial layer are left exposed, the parts of the front surface of the second epitaxial layer left exposed being accessible to the metal particles, the anode structure and the second epitaxial layer forming a first Schottky contact;
applying a biasing voltage to the detector, which cause the detector to generate a current that depends upon the concentration of the metal particles of the first material on the parts of the front surface of the second epitaxial layer left exposed; and
determining a first estimate based on said current, the first estimate indicating the concentration of the metal particles of the first material on the parts of the front surface of the second epitaxial layer left exposed.

11. The method according to claim 10, further comprising varying the biasing voltage applied to the detector, which cause said current to have a corresponding profile as a function of the biasing voltage, said profile including a first variable threshold having a position that depends upon the concentration of the metal particles of the first material on the parts of the front surface of the second epitaxial layer left exposed;
determining a first quantity indicative of the position of the first variable threshold; and
determining said first estimate as a function of said first quantity.

12. The method according to claim 11, further comprising storing calibration data that associate sample values of concentration with corresponding sample threshold values; and wherein determining said first estimate comprises comparing said first quantity with said calibration data.

13. The method according to claim 11, wherein:
arranging the detector in contact with the metal particles of a first material comprises forming a second Schottky contact between said metal particles of the first material and the parts of the front surface of the second epitaxial layer left exposed, said first variable threshold being a function of said second Schottky contact; and
said profile includes a fixed threshold, which depends upon said first Schottky contact and is equal to a value of biasing voltage higher than the first variable threshold.

14. The method according to claim 13, further comprising:
arranging the detector in contact with metal particles of a second material and forming a third Schottky contact between said metal particles of the second material and the parts of the front surface of the second epitaxial layer left exposed, said profile including a second variable threshold having a position that depends upon a concentration of the metal particles of the second material on the parts of the front surface of the second epitaxial layer left exposed;
determining a second quantity indicative of the position of the second variable threshold; and
determining a second estimate as a function of the second quantity, the second estimate being indicative of a concentration of the metal particles of the second material on the parts of the front surface of the second epitaxial layer left exposed.

15. A system for detecting a concentration of metal particles of a first material, the system comprising:
a detector including:
a contact;
a semiconductor body on the contact, the semiconductor body including:
a substrate;
a first epitaxial layer on the substrate, the first epitaxial layer being a doped layer having a first thickness; and
a second epitaxial layer on the first epitaxial layer and including a cathode region and a front surface, the second epitaxial layer being a doped layer having a second thickness greater than the first thickness; and
an anode structure of a conductive material, the anode structure including a plurality of anode regions that extend on and in physical contact with parts of the front surface of the second epitaxial layer, wherein the plurality of anode regions have the same orientation and are laterally staggered such that parts of the front surface of the second epitaxial layer are left exposed, wherein the anode structure and the second epitaxial layer form a Schottky contact, the parts of the front surface of the second epitaxial layer left exposed are accessible to the metal particles, and the detector is configured to generate an electrical quantity that depends upon a concentration of the metal particles of the first material on the parts of the front surface of the second epitaxial layer left exposed; and
a processing unit electrically coupled to the detector and configured to determine, based on the electrical quantity, the concentration of the metal particles of the first material on the parts of the front surface of the second epitaxial layer left exposed.

16. The system according to claim 15, wherein:
the electrical quantity has a profile that includes a first variable threshold having position that depends upon the concentration of the metal particles of the first material on the parts of the front surface of the second epitaxial layer left exposed; and
the processing unit is configured to determine a first quantity indicative of the position of the first variable threshold and to determine said concentration as a function of said first quantity.

17. The system according to claim 16, wherein the processing unit is configured to store calibration data that associate sample values of concentration with corresponding sample threshold values, and to compare said first quantity with said calibration data.

18. The system according to claim 16, wherein the profile of the electrical quantity also includes a fixed threshold, which depends upon said Schottky contact and is equal to a value of a biasing voltage greater than the first variable threshold.

19. The system according to claim 16, wherein:
the profile of the electrical quantity includes a second variable threshold in the presence of metal particles of a second material, the second variable threshold having a position that depends upon a concentration of the metal particles of the second material on the parts of the front surface of the second epitaxial layer left exposed; and
the processing unit is configured to determine a second quantity, indicative of the position of the second variable threshold, and determine, as a function of the second quantity, the concentration of metal particles of the second material on the parts of the front surface of the second epitaxial layer left exposed.

20. The system according to claim 15, wherein the cathode region is formed by a material chosen from among: silicon carbide, gallium nitride, silicon, or gallium aluminum nitride.

21. The system according to claim 1, wherein the detector includes a multilayer structure including a plurality of conductive layer, and the contact is on the multilayer structure.

22. The system according to claim 1, wherein the first epitaxial layer has a first doping level, and the second epitaxial layer has a second doping level different from the first doping level.

23. The system according to claim 1, wherein the contact includes:
a multilayer structure including a plurality of conductive layers; and
a contact region of a conductive material on the multilayer structure, the semiconductor body being spaced from the multilayer structure by the contact region.

* * * * *